United States Patent [19]
Cohen et al.

[11] Patent Number: 5,486,181
[45] Date of Patent: Jan. 23, 1996

[54] ACETABULAR CUP, METHOD AND TOOL AND INSTALLING THE SAME

[75] Inventors: Robert C. Cohen, Rockaway Township; Rafial Zubok, Midland Park, both of N.J.

[73] Assignee: Implex Corporation, Allendale, N.J.

[21] Appl. No.: 286,003

[22] Filed: Aug. 4, 1994

[51] Int. Cl.$^6$ ............................. A61F 2/46; A61B 17/88
[52] U.S. Cl. ............................. 606/91; 606/99; 606/100; 623/22
[58] Field of Search ............................. 606/91, 99, 100, 606/86; 623/22

[56] References Cited

U.S. PATENT DOCUMENTS

| | | | |
|---|---|---|---|
| 4,716,894 | 1/1988 | Lazzeri et al. | 606/91 |
| 5,098,437 | 3/1992 | Kashuba et al. | 606/89 |
| 5,108,448 | 4/1992 | Gautier | 623/22 |
| 5,169,399 | 12/1992 | Ryland et al. | 606/99 |
| 5,171,243 | 12/1992 | Kashuba et al. | 606/86 |
| 5,171,313 | 12/1992 | Salyer | 606/99 |
| 5,310,408 | 5/1994 | Schryver et al. | 623/22 |

*Primary Examiner*—David H. Willse
*Assistant Examiner*—Bruce E. Snow
*Attorney, Agent, or Firm*—Plevy & Associates

[57] ABSTRACT

An acetabular cup having an outer shell of a hard material defining a cavity circumscribed by an annular surface, and a bearing insert of a material which is softer than the material of the outer shell, the bearing insert being disposed within the cavity of the shell, and coupling tracks disposed on the annular surface for coupling a tool to the outer shell, the tool being used for installing the cup in a patient's acetabulum, the coupling tracks operating to prevent the tool from damaging the bearing insert during the installation of the cup. The tool for installing the acetabular cup of the present invention, comprises a handle for aligning and driving the acetabular cup into a patient's acetabulum which control the rotational, pivotal and axial alignment and an adaptor for coupling the handle to the acetabular cup, the adaptor having leg members for engaging the corresponding coupling tracks positioned on the annular surface of the outer shell when the leg members are brought into contact with the annular surface of the outer shell and the adaptor is rotated relative to the acetabular cup.

5 Claims, 11 Drawing Sheets

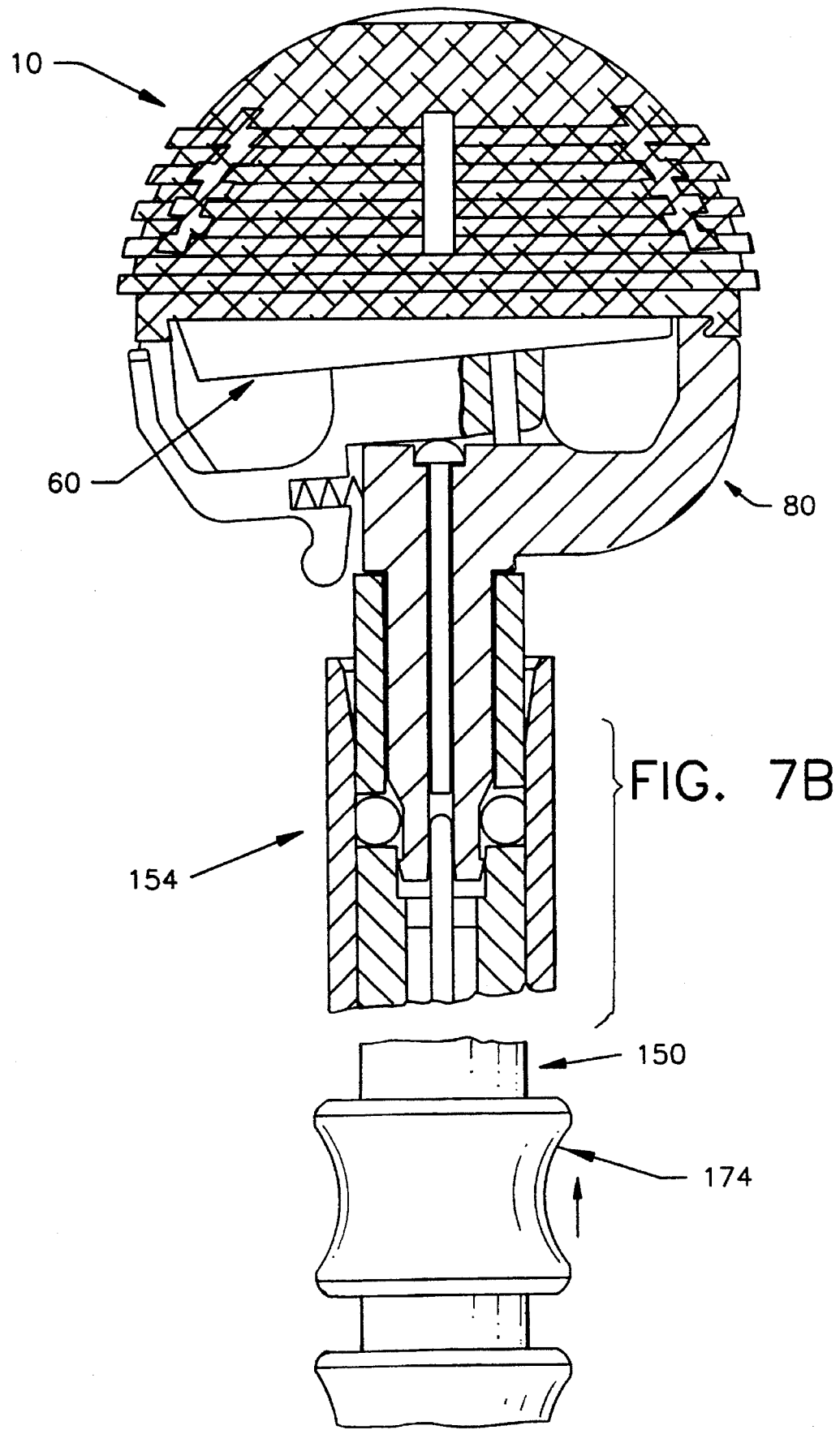

ACETABULAR CUP, METHOD AND TOOL AND INSTALLING THE SAME

FIELD OF THE INVENTION

The present invention relates generally to an improved prosthetic device, and more particularly to an improved acetabular cup assembly and method which facilitates implanting the cup in a patient's acetabulum as a fully assembled unit. Additionally, the invention relates to a tool for installing the acetabular cup assembly of the present invention.

BACKGROUND OF THE INVENTION

To allow a wide range of motion at the hip, the joint is configured as a ball and socket arrangement. These joints provide for a wide range of motion. In a hip joint, the femoral head is joined to the proximal femur by a neck which is angularly disposed relative to the axis of the femur. The natural socket or acetabulum located in the pelvis, receives the femoral head and cooperates with it to form a joint which permits relative motion. Deterioration of the acetabulum and/or femoral head can be brought about by injury or various progressive diseases such as osteoarthritis. When injury or disease occurs, the damaged component can be replaced or rebuilt using an appropriate prosthetic device. Various techniques have been developed over the years for replacing injured or deteriorated joint components. In the technique known as a "total hip replacement", one method involves cementing or press-fitting a cup into the acetabulum. In this technique, the entire natural femoral head and neck are removed and a femoral prosthetic device comprising an elongated stem, a neck and a bearing head is implanted within the proximal femur.

In any event, acetabular implants are well known in the an for replacing the socket portion of a patient's hip joint. Typical acetabular cup assemblies comprise a metal cup shell which are adapted to be secured within the patient's acetabulum, and an inner liner of plastic material which provides a spherical bearing surface for receiving the femoral bearing head portion of the femoral prosthetic device. The metal cup shell may be provided with an external thread arrangement to facilitate anchoring to the pelvic bone or it may be secured by other means such as cement, screws or simply an interference fit. The plastic insert can be secured within the metal cup in a variety of methods which include using retaining rings, press fitting or force fitting the plastic insert into the interior of the metal cup and/or thermally fitting the plastic insert into the interior of the metal cup.

A particular problem that can occur with prior art acetabular cup designs is that they can be damaged by the tools used for impacting or driving them into the acetabulum. This is especially true regarding acetabular cup designs having the plastic bearing insert already installed into the metal shell prior to the cup being implanted into the acetabulum.

In partial or total hip replacement surgery utilizing this type of acetabular cup, the surgeon places the impaction tool used for positioning and driving the cup into the acetabulum, onto the metal shell or onto the plastic insert.

In the case where the tool is placed on the metal shell slippage of the impaction tool can occur if the metal shell has no provision for receiving the impaction tool. If the impaction tool slips off the metal shell it can damage the plastic bearing insert. Once the bearing insert is damaged, the surgeon may have to replace it and/or remove and replace the entire cup which is quite costly and time consuming. Moreover, since the impaction tool is not securely coupled to the acetabular cup, it may be difficult to properly orient the acetabular cup in the acetabulum during impaction. This presents a serious problem because in order to realize maximum performance from this surgical procedure, the acetabular cup must be properly positioned in the acetabulum. If the acetabular cup is incorrectly implanted, dislocations of the hip joint, decreased range of motion, and eventual loosening or failure of the prosthetic components can occur.

In the case where the impactor tool is placed onto the plastic insert, the impactor may cause permanent deformation and provide for less than optimum contact with the femoral prosthetic bearing head. This can result in accelerated generation of poly debris due to poor contact and a disturbance of the plastic insert locking mechanism.

The present invention overcomes these problems by providing means for coupling a specially designed cup impactor tool to the acetabular cup.

It is, therefore, an object of the present invention to provide an improved acetabular cup design, method and tool for installing the cup which allows the acetabular cup to be installed in the correct orientation and as an assembled unit without damaging the plastic bearing insert.

SUMMARY OF THE INVENTION

The present invention comprises an acetabular cup having an outer shell of a hard material defining a cavity circumscribed by an annular surface, and a bearing insert of a material which is softer than the material of the outer shell, the bearing insert being disposed within the cavity of the shell, and coupling means disposed on the annular surface for coupling a tool to the outer shell, the tool being used for installing the cup in a patient's acetabulum, the coupling means operating to prevent the tool from damaging the bearing insert during the installation of the cup.

The present invention further includes a method for implanting the acetabular cup of the present invention into a patients's acetabulum, the method comprising the steps of preparing the acetabulum to receive the cup, attaching an installation tool to tool coupling means on the outer shell of the cup, aligning the cup within the acetabulum using the installation tool which provides for a means to control rotation, axial alignment impacting direction, and pivotal orientation, driving the cup into the acetabulum using the installation tool, and detaching the installation tool from the outer shell by actuating a tool releasing means located on the installation tool.

The present invention also includes a tool for installing the acetabular cup of the present invention, comprising handle means for aligning and driving the acetabular cup into a patient's acetabulum, adaptor means for coupling the handle means to the acetabular cup, the adaptor means having leg means for engaging corresponding leg receiving means positioned on the peripheral surface of the outer shell when the leg means are brought into contact with the peripheral surface of the outer shell and the adaptor is rotated relative to the acetabular cup.

BRIEF DESCRIPTION OF THE FIGURES

FIG. 7B shows how the cup adaptor/impactor tool of FIG. 7A is disengaged from the acetabular cup.

DETAILED DESCRIPTION OF THE INVENTION

Figure 1:
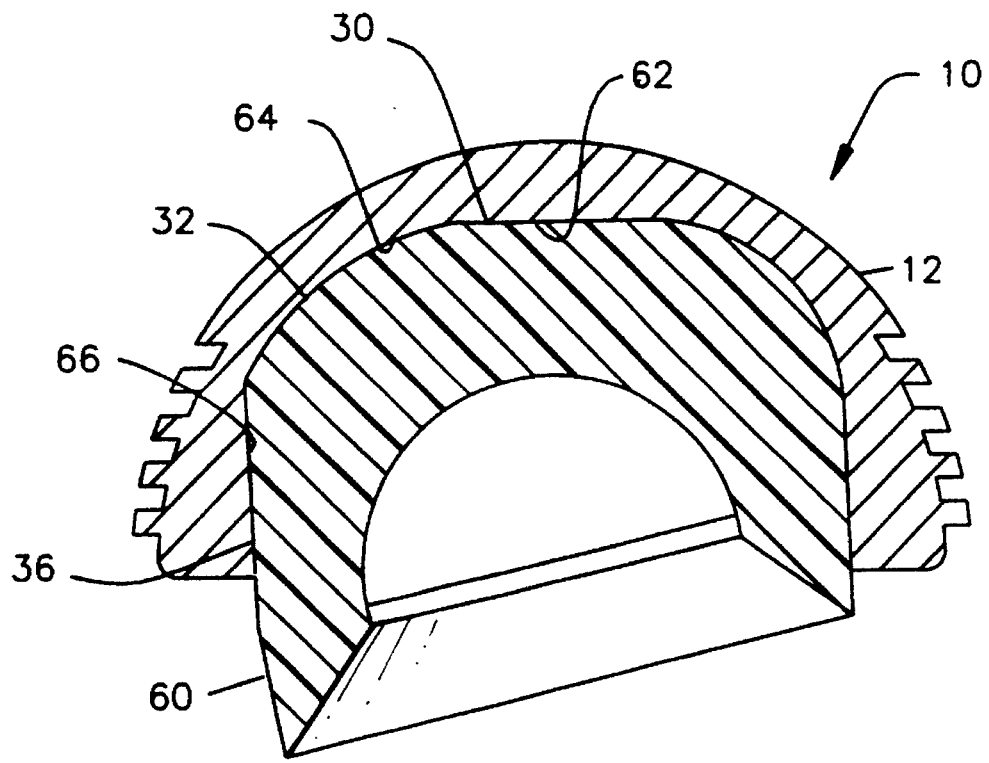
FIG. 1 is a cross-sectional view of a preferred exemplary embodiment of the acetabular cup of the present invention, (impactor tool coupling means not visible in this view)

Referring to FIG. 1, there is shown a cross-sectional view of a preferred embodiment of an acetabular cup according to the present invention designated by the numeral 10. Generally, the acetabular cup 10 is a two component assembly comprising a shell component 12 and a bearing insert 60 which has been assembled within the shell component 12. Preferably, the shell component 12 is made from a metal such as titanium or cobalt-chrome alloy, however, any material which is compatible with the bone and body tissues of the patient can be used. The bearing insert 60 is preferably made from a plastic material such as polyethylene or any other like biocompatible bearing material which has sufficient strength and wear resistance.

Figure 2A:
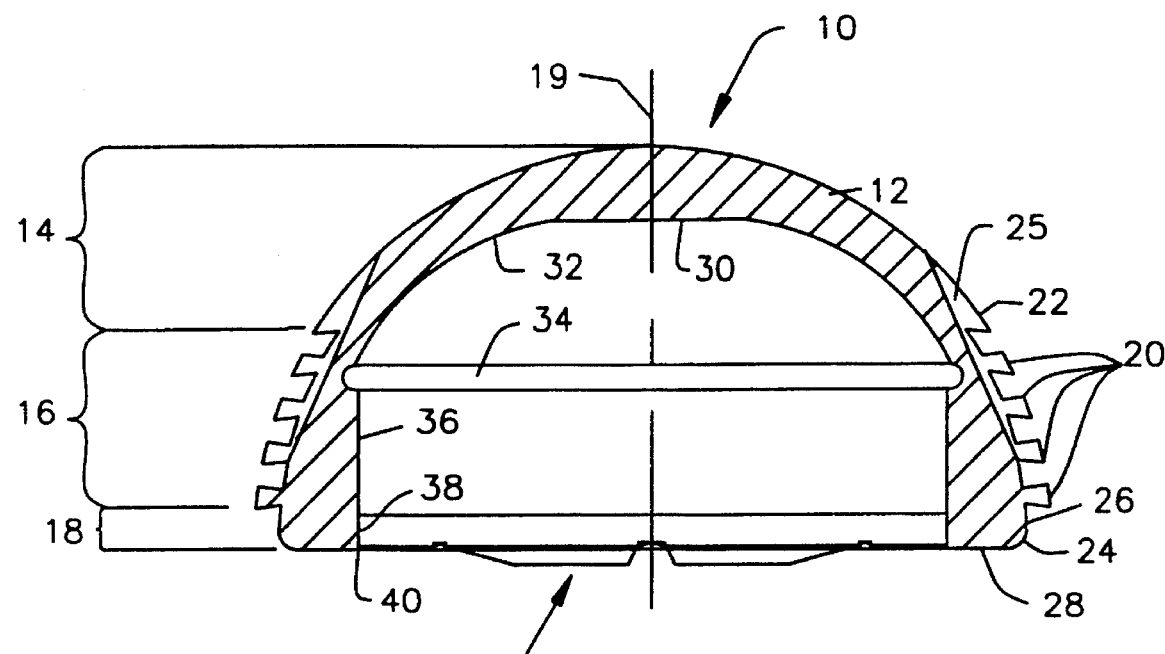
FIG. 2A is a cross-sectional view of the outer shell member of the acetabular cup of FIG. 1 with the bearing insert removed.

The structure of the shell component 12 will now be described in greater detail with reference to FIG. 2A. As can be seen, the exterior of the shell component 12 comprises an apical region 14, a rim region 16, and a small base region 18.

The surface curvature of the apical region 14 is preferably ellipsoidal, however, any suitable profile such as hemispherical or the like, is contemplated. Acetabular cups having ellipsoidal surface curvatures are described in U.S. patent application Ser. No. 08/052,248 entitled PROSTHETIC ACETABULAR CUP AND METHOD OF IMPLANT, filed on Apr. 22, 1993 by Robert Averill et al. and assigned to Implex Corporation, the assignee herein, the disclosure of which is incorporated herein by reference.

A plurality of locking ribs 20 are provided along the rim region 16 of the shell component 12. The locking ribs 20 are arranged in parallel rows and are coaxially positioned around the mid-axis 19 of the shell component 12. A transition rib 22 is disposed on the shell component 12 at the top of rim region 16. The transition rib 22 is also arranged in parallel with the locking ribs 20 and is co-axially positioned around the mid-axis 19 of the shell component 12. Preferably, each of the locking ribs 20 have a generally dove tail shape profile in cross-sectional the details of which are also described in U.S. patent application Ser. No. 08/052,248.

The base region 18 of the shell component 12 includes a vertical surface 26 that extends below the lower most locking rib 20 to a chamfered edge 24. Chamfered edge 24 joins the vertical surface 26 to the horizontal annular base surface 28 of the shell component 12.

Disposed on the horizontal annular base surface 28 are impactor tool coupling means. In the preferred embodiment shown in FIGS. 2A–2E, the impactor tool coupling means comprises a pair of locking tracks 42A and 42B. The locking tracks are disposed approximately 180 degrees apart on the horizontal annular base surface 28 of the acetabular cup as shown in FIGS. 2D and 2E. It should be understood, however, that any suitable number of locking tracks can be provided on the annular base surface of the acetabular cup. Moreover, many variations in the structure of the locking tracks shown in the preferred embodiment of FIGS. 2A–2E, are possible.

Figure 2B:
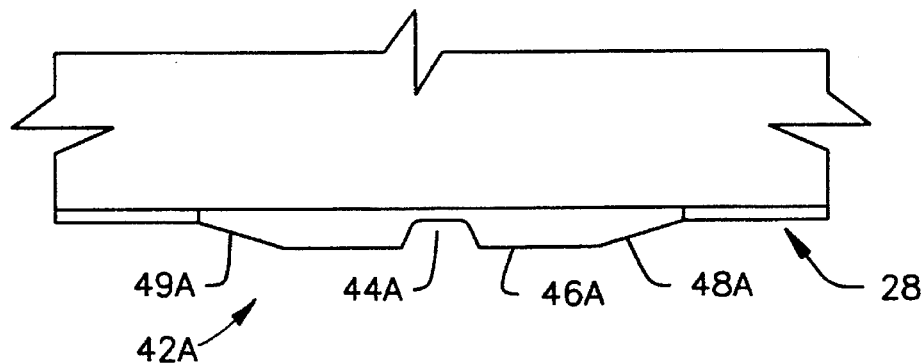
FIG. 2B is an enlarged view of the locking track shown in FIG. 2A.
Figure 2C:
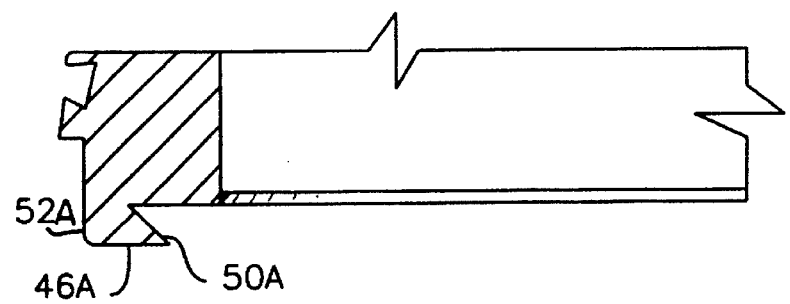
FIG. 2C is a cross-sectional view through the locking track shown in FIG. 2B.
Figure 2D:
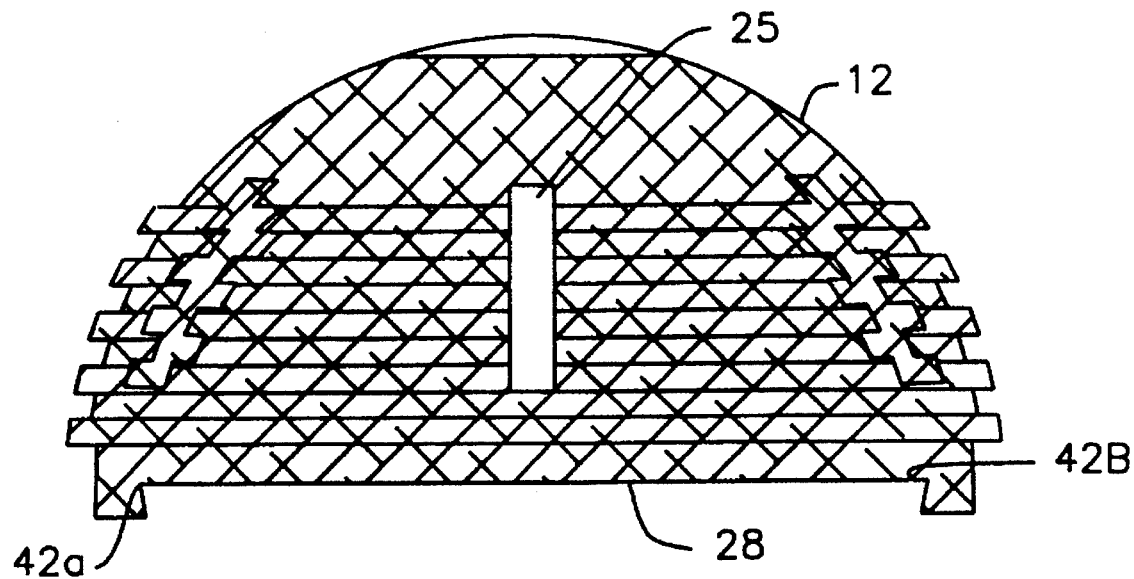
FIG. 2D is a side plan view of the outer shell member shown in FIG. 2A.
Figure 2E:
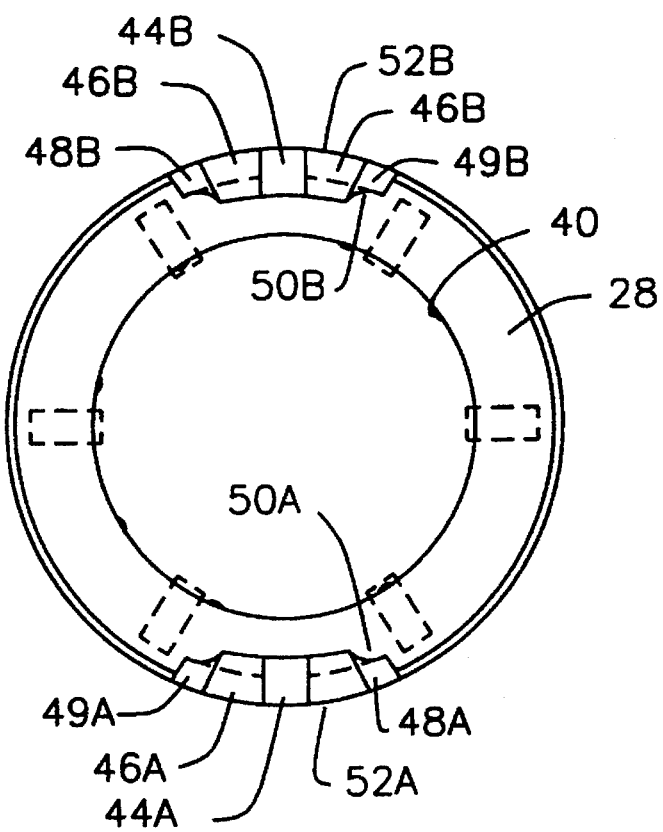
FIG. 2E is a bottom plan view of the outer shell member of FIG. 2A.

Referring now to FIG. 2B, which shows an enlarged view of locking track 42A and FIG. 2E which shows both locking tracks 42A and 42B, the locking tracks will now be described in detail. Locking track 42A includes a first inclined ramp surface 48A which emerges from the horizontal annular base surface 28 and extends circumferentially into a track rim surface 46A. The track rim surface 46A extends circumferentially in parallel relationship to the horizontal annular base surface 28 and includes a depression 44A. The track rim surface 46A terminates at a second inclined ramp surface 49A which merges back into the horizontal annular base surface 28.

Similarly, as is visible in FIG. 2E, locking track 42B includes a first inclined ramp surface 48B which emerges from the horizontal annular base surface 28 and extends circumferentially into a track rim surface 46B. The track rim surface 46B extends circumferentially in parallel relationship to horizontal annular base surface 28 and includes a depression 44B. The track rim surface 46B terminates at a second inclined ramp surface 49B which merges back into the horizontal annular base surface 28. Referring to FIG. 2C, locking track 42A further includes an inner undercut surface 50A and an outer surface 52A which is a continuation of vertical surface 26.

The locking tracks operate to allow the acetabular cup to be securely coupled to the impactor tool at the outer periphery of the shell component 12. This configuration assures that the impactor tool will not damage the bearing insert of the acetabular cup as it substantially eliminates slippage between the shell component and the impactor tool during the installation of the cup. Further, the secure coupling of the acetabular cup to the impactor tool allows the surgeon to precisely orient the acetabular cup in the patient's acetabulum, thus maximizing the performance of the prosthesis.

Moving now to the interior of the shell component 12 and with reference again to FIG. 2A, there is shown an apex region 30 which presents a flat surface. Descending from the flat apex region 30 is a spherically curved surface 32. The bottom of the spherically curved surface 32 terminates at an annular groove 34 formed in the shell component 12. Moving below annular groove 34 is a converging engagement wall 36. A vertical wall 38 extends from the bottom of the converging engagement wall 36. The vertical wall 38 is parallel to mid-axis 19. Locking projections 40 extend inwardly from the bottom of the vertical wall 38 proximate the horizontal annular base surface 28 of the shell 12.

Figure 3:
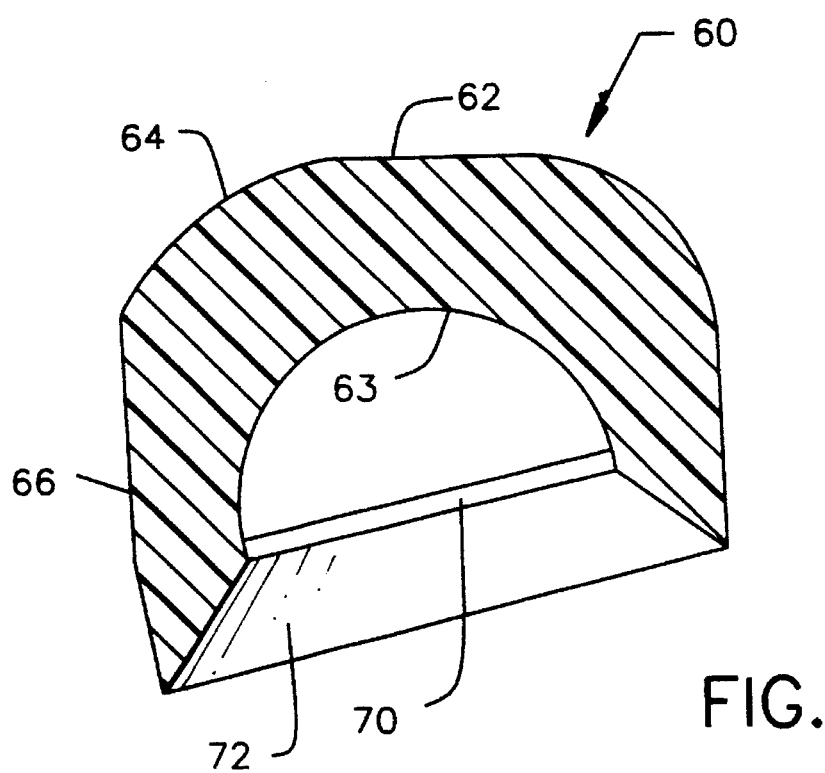
FIG. 3 is a cross-sectional view through the bearing insert which is installed in the acetabular cup shown in FIG. 1.

Referring to FIGS. 1 and 3, it can be seen that the bearing insert 60 generally conforms to the inner surface of the shell component 12. Accordingly the flat top region 62 of the bearing inserts 60 lays flush against the flat apex region 30 within the shell component 12. Similarly, the spherically curved region 64 of the bearing insert 60 conforms to the spherically curved surface 32 within the shell component 12. The inclined surface 66 of the bearing insert 70 lies against the converging engagement wall 36 of the shell component 12. Although the bearing insert 60 may be pressed into the shell component 12 the preferred method of assembly consists of cold inserting bearing insert 60 within the shell component 12 by creating a temperature differential between the bearing insert 60 and the shell 12 prior to insertion. By cooling the bearing insert and/or heating the shell component the bearing insert can be inserted into the shell without an interference. Upon an equilibrium in temperature between the bearing insert and the shell, an interference fit occurs across all surfaces and the locking projections cut into the material of the bearing insert locking the bearing insert into a set position relative to the shell component 12.

Screw holes 25 as shown in FIG. 2D may be provided in the shell component 12 to aid in securing the shell component in the acetabulum. The exterior surface of the shell component 12 can also include a sintered porous coating of beads made from cobalt chromium or the like which provides for the ingrowth of bone material into the surface of the shell component to further secure the shell component in the acetabulum.

As earlier mentioned, the acetabular cup 10 is installed by coupling it to a novel impactor tool. This is accomplished by coupling a specially designed cup adaptor between the impactor tool and the acetabular cup 10. This method allows differently sized acetabular cups to be installed using the same impactor tool. This is facilitated by varying the size of the cup adaptors to match and fit a particular sized acetabular cup. The impactor tool coupling portion of each cup adaptor, however, is universally sized so that only one impactor tool required. The cup adaptors are color coded to match the color code on their respective acetabular cups. Further, unlocking means are provided in the cup adaptor of the present invention which coact with corresponding unlocking means provided on the impactor tool (to be described later on), which allow the cup adaptor to be remotely uncoupled from the acetabular cup by actuating the unlocking means provided on the impactor tool.

In any event, a preferred embodiment of the cup adaptor will now be described, although, many other embodiments of the cup adaptor are possible and will become apparent from the foregoing description.

Figure 4A:
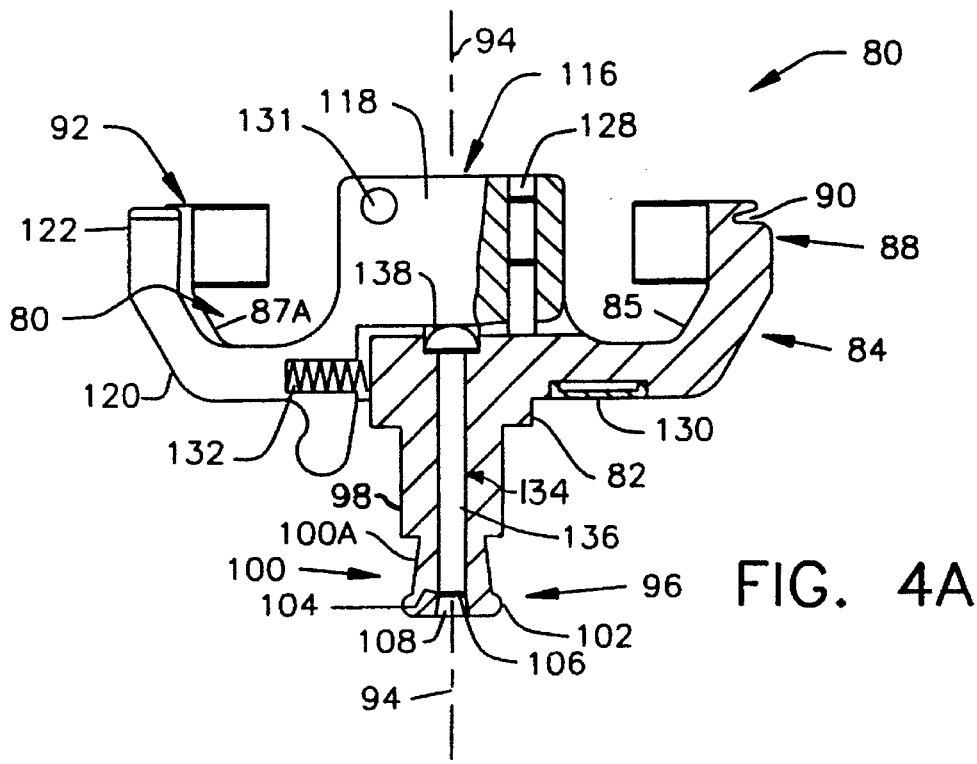
FIG. 4A is a cross-sectional view through a preferred exemplary embodiment of the cup adaptor of the present invention.

Referring to FIG. 4A, there is shown a cup adaptor according to a preferred embodiment of the present invention designated by the numeral 80. Cup adapter 80 comprises an adapter body 82 have a centrally disposed axis 94. Extending radially away in opposite directions from adapter body 82 are leg 84 and split leg 86. Leg 84 comprises an outwardly extending member 85 and a track coupling section 88. The outwardly extending member 85 extends radially away from the adaptor body 82. Located at the outer-most portion of outwardly extending member 85 is the track coupling section 88 which includes a track coupling groove 90.

Similarly split leg 86 includes a pair of parallel oriented outwardly extending members 87A and 87B (87B not visible in FIG. 4A) which extend radially away from the adaptor body 82. Located at the outer-most portion of the outwardly extending members is and a track coupling section 92. As shown in FIGS. 4D and 4E, track coupling section 92 comprises of a pair of track coupling sections 93A and 93B which correspond to outwardly extending members 87A and 87B. Each track coupling section 93A and 93B defines a respective track coupling groove 95A and 95B.

Referring again to FIG. 4A, cup adaptor 80 further comprises a radially extending pivoting locking leg 116 which extends parallel to and follows the contour of split leg 86. The pivoting locking leg 116 comprises a body portion 118 which pivotally couples the locking leg 116 within the adaptor body 82 via a pivot pin 131. An outwardly extending member 120 extends radially away from body 118. Disposed at the outer-most end of outwardly extending member 120 is a locking pin 122.

An impactor coupling chuck 96 extends from adaptor body 82 along axis 94. Chuck 96 comprises cylindrical member 98. An annular groove 100 is disposed at the marginal end of cylindrical member 98. Groove 100 defines an annular surface 100A which tapers outwardly toward the outer most end of cylindrical member 98. Groove 100 merges into an annular locking flange 102 which is provided at the outer most end of cylindrical member 98. The outer most edge of flange 102 presents a chamfered surface 104.

Chuck 96 further includes a bore 106 which extends entirely through chuck 96 into the adaptor body 82 where it communicates with a larger bore (not visible in FIG. 4A). The opening on the chuck side of bore 106 includes a tapered surface 108 which tapers inwardly in the direction of the adaptor body 82.

A pivoting leg actuating pin 134 resides partially within bore 106 and comprises a shaft portion 136 which is capable of reciprocal movement within bore 106, and a head portion 138. Actuating pin 134 is designed to engage the body portion 118 of the pivoting locking leg 116 via head 138 thereby causing the pivoting locking leg 116 to pivot on pivot pin 131 from a locked position to an unlocked position the purpose of which will become apparent in the foregoing.

A spring 132 acting between adapter body 82 and the outwardly extending member 120 of the pivoting locking leg 116, returns the pivoting locking leg 116 to the locked position when the actuating pin returns and disengages the pivoting locking leg 116.

A set screw 128 is provided in body 118 of the pivoting locking leg 116 to allow the locking position of the pivoting locking leg 116 to be fine tuned and adjusted.

A colored insert 130 is provided on the surface of the adapter body 82 for the purpose of identifying the particular size of the cup adapter 80. As mentioned earlier, the cup adaptor is sized to correspond to a particular sized acetabular cup assembly.

Figure 4B:
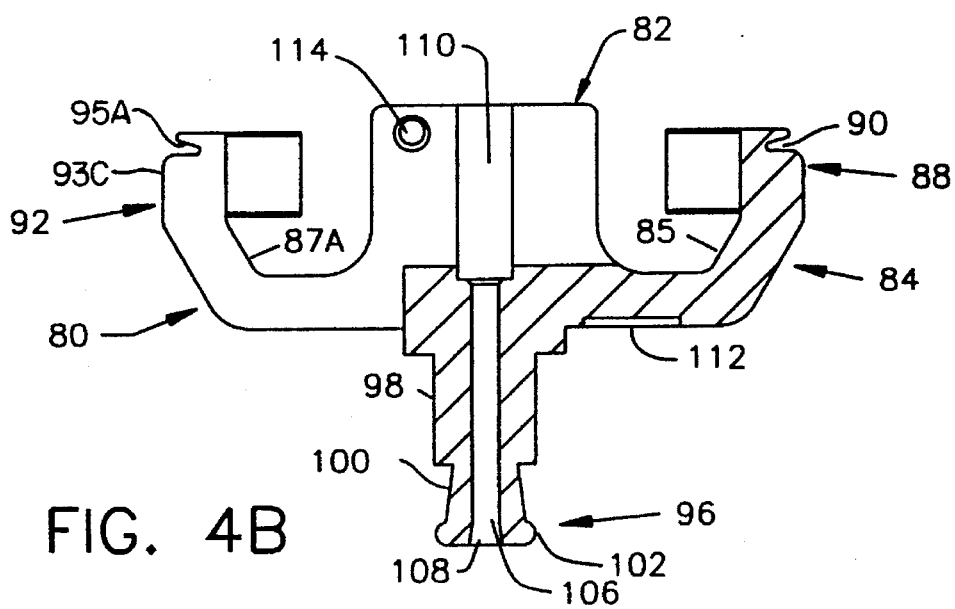
FIG. 4B is a cross-sectional view through the body of the cup adaptor shown in FIG. 4A.

FIG. 4B shows the adapter body 82 without the pivoting locking leg 116 installed. As can be seen, a bore 110 is provided in the adaptor body 82 and communicates with smaller bore 106. The larger diameter of bore 110 allows the actuating pin 134 to be assembled into the adapter body while also providing a space for linear reciprocating motion of the head of the actuating pin 134 within the adaptor body 82 as will be explained further on.

Also visible in FIG. 4B is one of the outwardly extending members 87A of split leg 86 and its associated track coupling section 93A and track coupling groove 95A. Further, recess 112 is provided in outwardly extending member 85 for the purpose of receiving the earlier mentioned indicia insert 130.

Figure 4C:
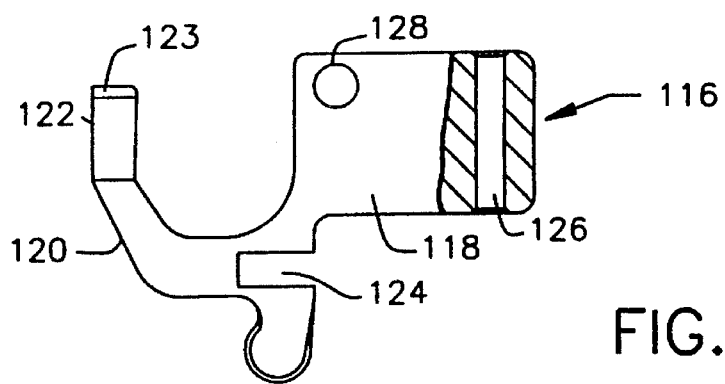
FIG. 4C is a partial cross-sectional view of the pivoting locking leg of the cup adaptor of FIG. 4A.
Figure 4D:
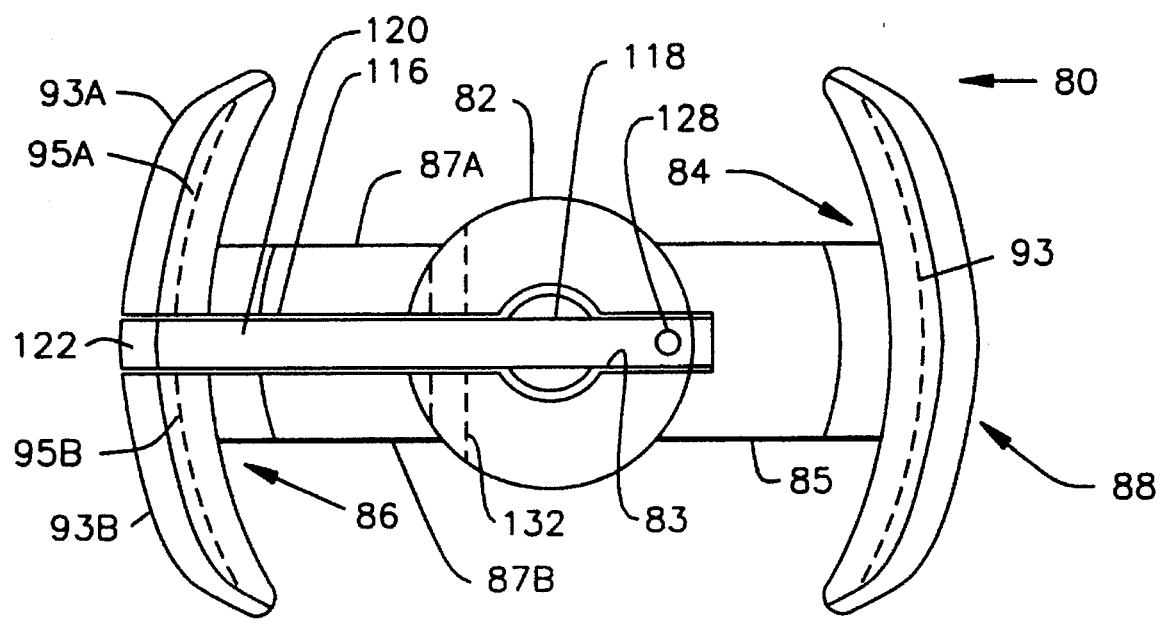
FIG. 4D is a bottom plan view of the cup adaptor shown in FIG. 4A.
Figure 4E:
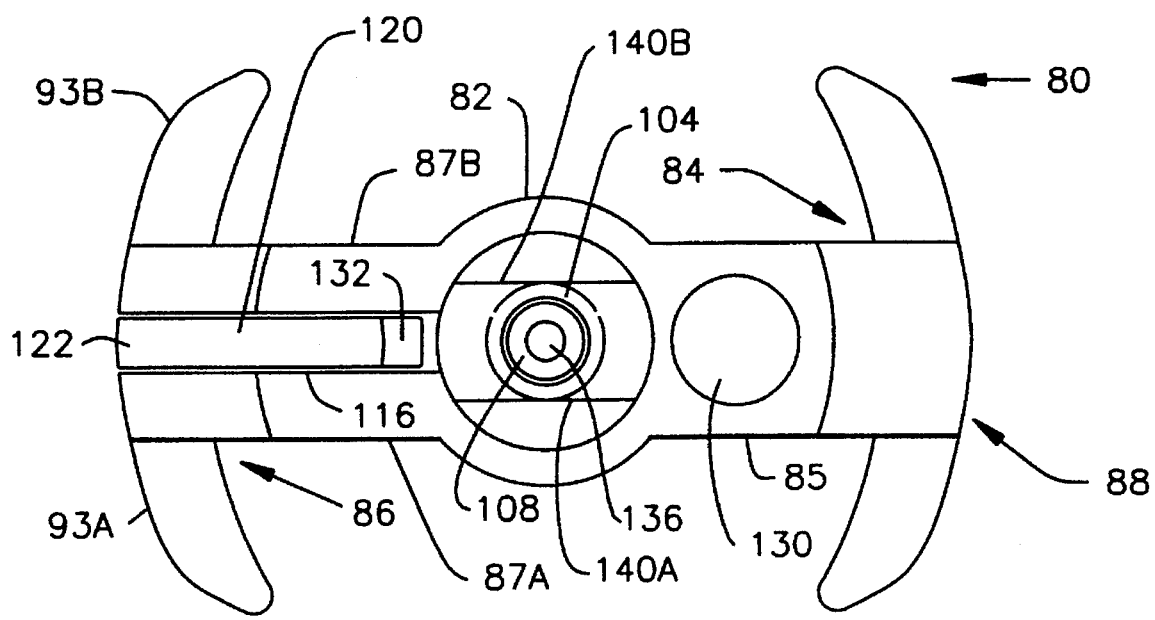
FIG. 4E is a top plan view of the cup adaptor shown in FIG. 4A.

In FIG. 4C, there is shown an enlarged illustration of the pivoting locking leg 116. The body 118 of the pivoting locking leg 116 includes a threaded bore 126 for receiving the set screw 128. Disposed on the opposite side of body 118 is an aperture 128 which receives pivot pin 131. The outwardly extending member 120 of pivoting locking leg 116 includes a spring seat 124 for receiving the pivoting locking leg return spring 132. At the free end of locking pin 122 is radiused at 123.

In FIGS. 4D and 4E, the outwardly extending member 85 and the track coupling section 88 of leg 84 form a generally T-shape structure. The track coupling 88 section forms an arc-like member. In FIG. 4D, the track coupling groove 90 extends in an arc-like manner and is shown in phantom by broken lines.

Figure 4F:
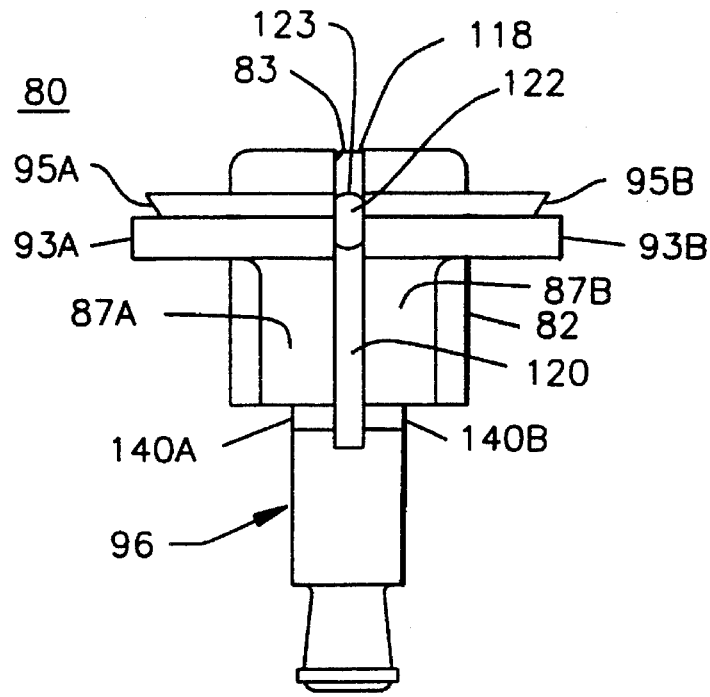
FIGS. 4F and 4G are side elevational views of the cup adaptor shown in FIG. 4A.

Similarly, split leg 86 and track coupling section 92 form a generally T-shape structure. The outwardly extending member 120 of the pivoting locking leg 116 is disposed between outwardly extending members 87A and 87B as shown in FIGS. 4D–4F. The track coupling sections 95A, 95B and locking pin 122 of pivoting locking leg 116, form an arc-like profile which is substantially identical to the arc-like profile of track coupling section 88. Further, the track coupling grooves 93A and 93B both extend in an arc-like manner in each of their respective track coupling sections as shown in phantom by the broken lines.

Figure 4G:
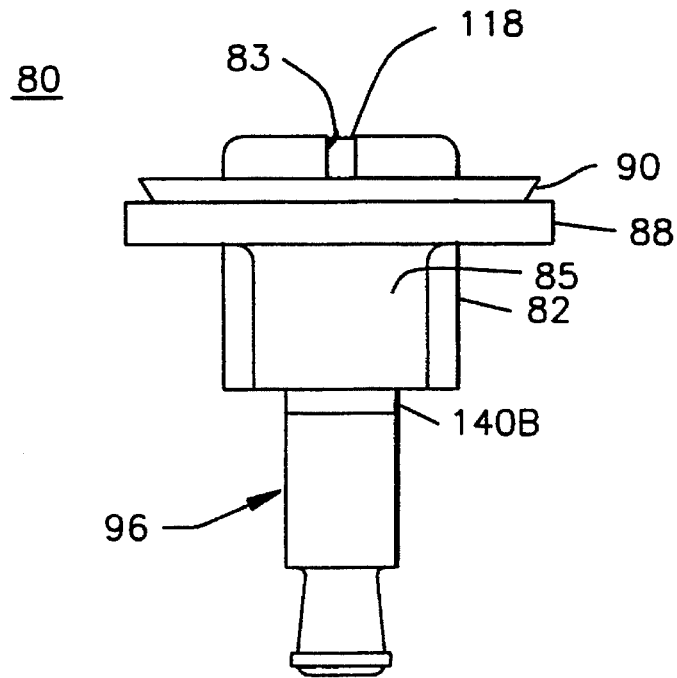

A slot 83, for receiving the body 118 of pivoting locking leg 116, is provided in a portion of the adaptor body 82 located immediately adjacent to the head 138 of the actuating pin 134 and communicates with bores 106 and 110 as shown in any of FIGS. 4D, 4F and 4G.

Flats 140A and 140B are provided on the adaptor body 82 in the area immediately adjacent to the base of the cylindrical member 98 as shown in any of FIGS. 4E, 4F or 4G. The function of these flats will soon become apparent.

As already mentioned, the present invention also consists of a specially designed impactor tool. When the impactor tool is used in conjunction with the earlier-described cup adaptor, it allows the surgeon to accurately position the acetabular cup of the present invention within the acetabulum and then drive the acetabular cup into place.

A preferred embodiment of the impactor tool hereinafter referred to as "IPT", will now be described with reference to FIGS. 5A–5E. It should become apparent to one of ordinary skill in the art, however, that many variations in the structure of the impactor are possible depending upon factors such as, the particular configuration of the cup adaptor, etc.

Figures 5A, 6D:
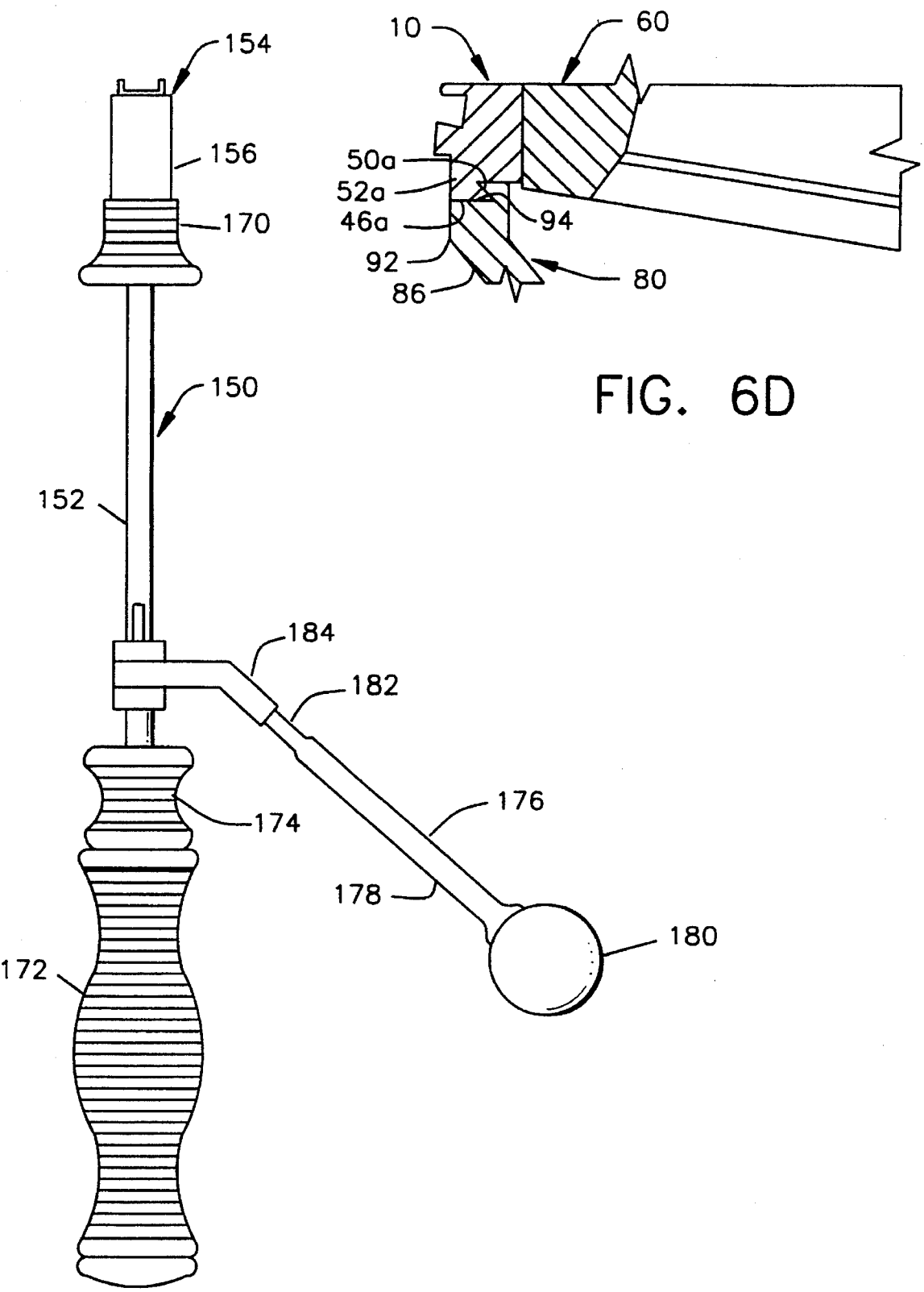
FIG. 5A is a plan view of the a preferred exemplary embodiment of the impactor tool of the present invention.
FIG. 6D is a cross-sectional view of FIG. 6A along line D—D.

Referring first to FIG. 5A, the IPT according to the present invention is designated by the numeral 150. The IPT 150 generally comprises a tubular shaft 152 having a first end and second end. The first end includes a chuck coupling means 154 having a reciprocating chuck release collar 156 and a collar grip 170.

The second end of the tubular shaft 152 comprises a hand grip 172 and a reciprocating cup release collar 174. Both the release collar 156 and the cup release collar are biased in the direction of the first end. IPT 150 further comprises an assist handle assembly 176 which is angularly attached to the tubular shaft immediately adjacent to cup release collar 174. The assist handle assembly comprises an assist handle shaft 178 having a grip 180 on one end and a tapered coupling 182 on the other end. The assist handle is removably attached to the tubular shaft 152 via assist handle receiving collar 184.

Figure 5B:
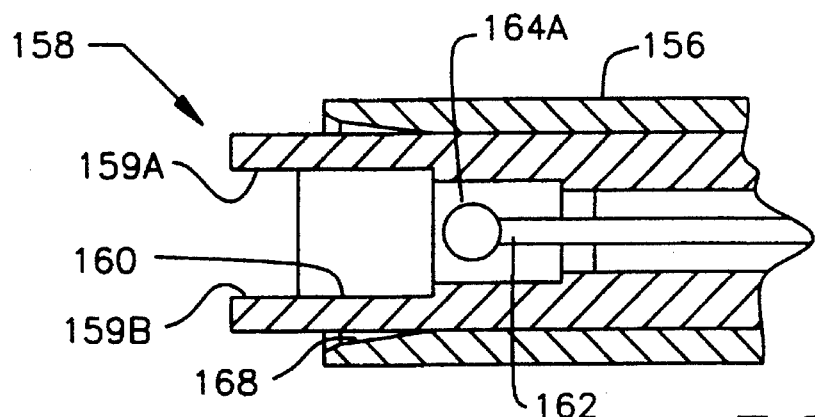
FIG. 5B is a cross-sectional view through the coupling means of the of the impactor tool shown in FIG. 5A.
Figure 5C:
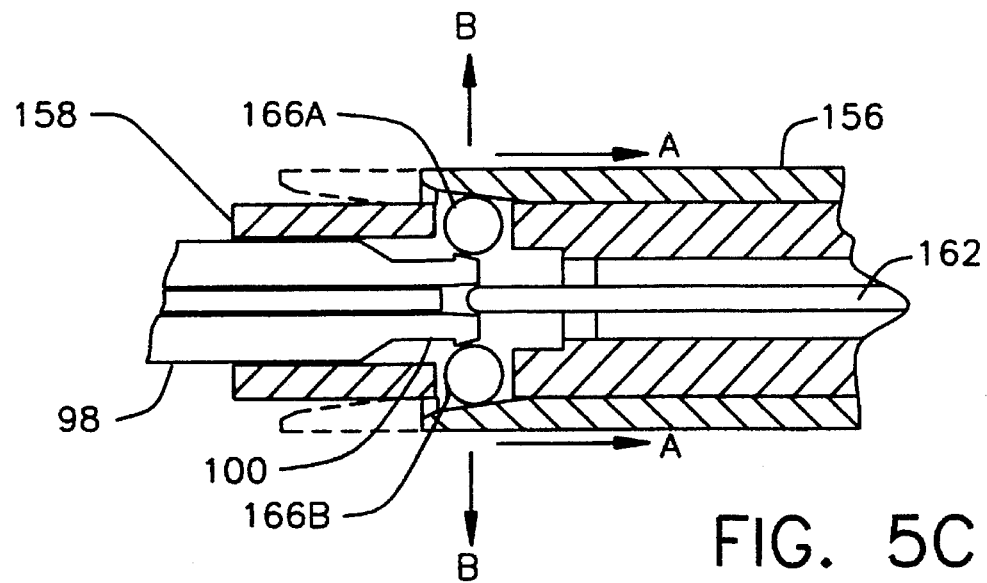
FIGS. 5C and 5D are cross-sectional views which show how the coupling means of the impactor tool couples to the chuck of the cup adaptor.
Figure 5D:
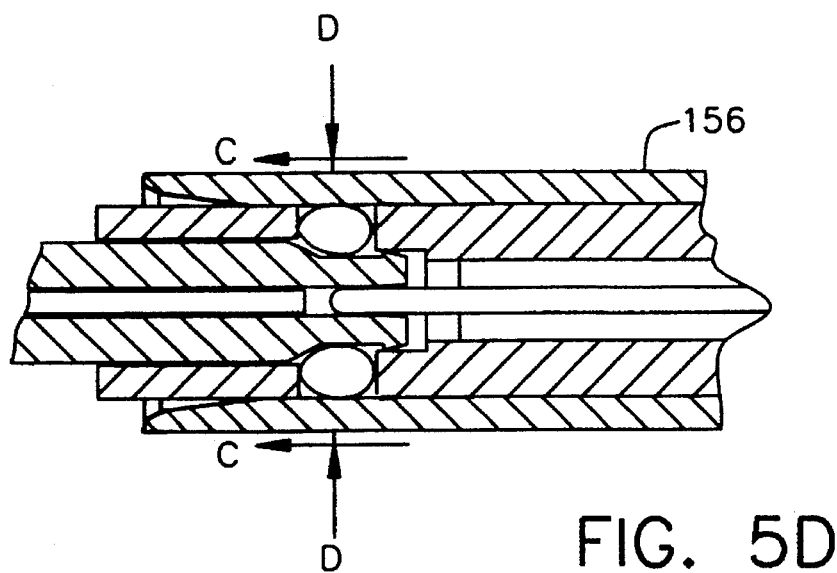

As shown in FIGS. 5B–5D, coupling means 154 comprises the free end 158 of tubular shaft 152 and includes anti-rotation keys 159A and 159B. A stepped bore 160 for receiving the cup adaptor chuck is provided in free end 158. Just beyond the stepped bore 160 in the marginal end of tubular shaft 152 are opposing locking ball apertures 166A and 166B. Apertures 166A and 166B receive locking balls 164A and 164B. The locking balls are held in the apertures by the chuck release collar 156 and a cup release rod 162. The cup release rod 162 extends through the tubular shaft 152 and couples with the cup release collar 174. An annular inclined inner surface 168 is provided at the free end of the chuck release collar 156.

A preferred method for installing the acetabular cup of the present invention using the impactor tool and cup adaptor of the present invention will now be described.

First, an appropriately sized acetabular cup is selected and then an appropriately sized cup adaptor is selected. The IPT is then coupled to the selected cup adaptor. To couple the cup adaptor to the IPT, one merely grasps and slides the collar grip 170 along the tubular shaft 152 in the direction of the hand grip 172 as shown in FIG. 5C. At the same time, the chuck 96 of the adaptor cup is inserted into the stepped bore 160 of the IPT. This causes the locking balls to engage chamfered edge 104 of locking flange 102 and travel through their respective locking ball apertures. The balls pass partially through the apertures into the space provided by the inclined inner surface 168 of the chuck release collar. When the cylindrical collar 98 is fully seated within stepped bore 160, the chuck release collar is released and snaps back to its original position. As the collar moves back to its original position, the inclined surface 168 forces the locking balls back through their apertures into groove 100 on the chuck of the cup adaptor thus locking the cup adaptor and IPT together. When fully coupled, the anti-rotation keys 159A and 159B of the IPT mate with flats 140A and 140B on the cup adaptor to prevent the IPT from rotating relative to the cup adaptor.

Once the cup adaptor and IPT are coupled together, the cup adaptor is coupled to the selected acetabular cup. The acetabular cup and cup adaptor are locked together by turning the cup adaptor along the base surface 28 of the cup so that the tracking coupling sections 90 and 92 of the cup adaptor run along the locking tracks 42A and 42B of the cup and lock into place in a bayonet locking arrangement as shown in sequence in FIGS. 6A–6D. Note that only the track coupling section 92 having the pivoting locking arm is shown in FIGS. 6A–6D. It should be understood, however, that track coupling section 90 engages its associated locking track 42B in virtually the same manner except for the operation of the locking pin.

Figure 6A:
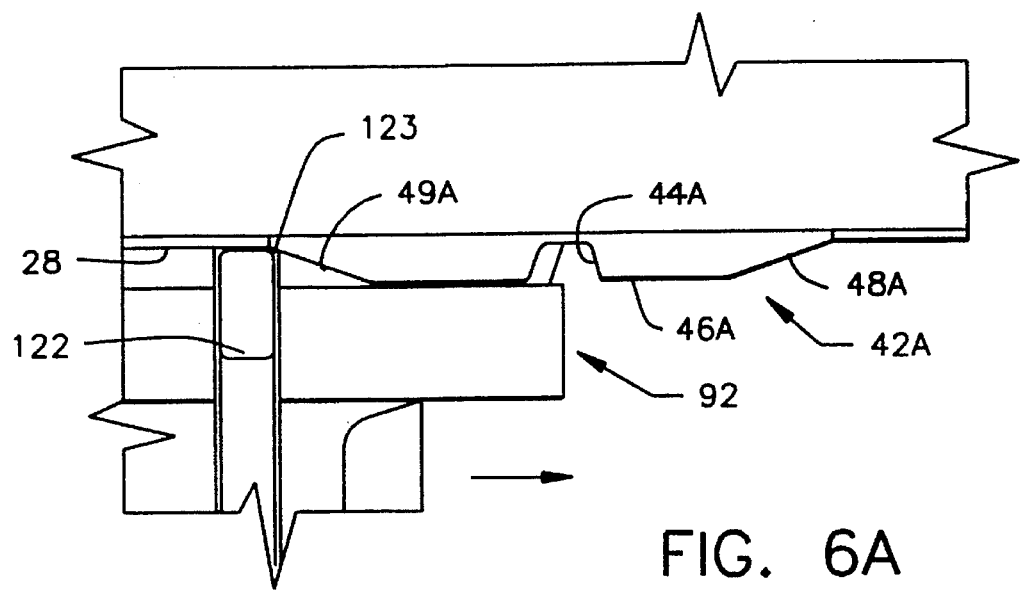
FIGS. 6A–6C show how the cup adaptor attaches to the locking track of the acetabular cup.

Accordingly, as track coupling section 92 engages locking track 42A, undercut inner surface 50A coacts with groove portion 94 as shown in FIG. 6D, to prevent axial separation of the cup from the cup adaptor. In FIGS. 6A and 6C, track receiving section 92 slides along locking track 42A.

Upon engagement, as seen in FIG. 6A, the locking pin 122 of the pivoting locking arm begins to ride up the inclined surface 49A from base surface 28. As locking pin 122 rides up the inclined surface 49A, the pivoting locking leg pivots into the unlocked position and compress the pivoting leg return spring.

Figure 6B:
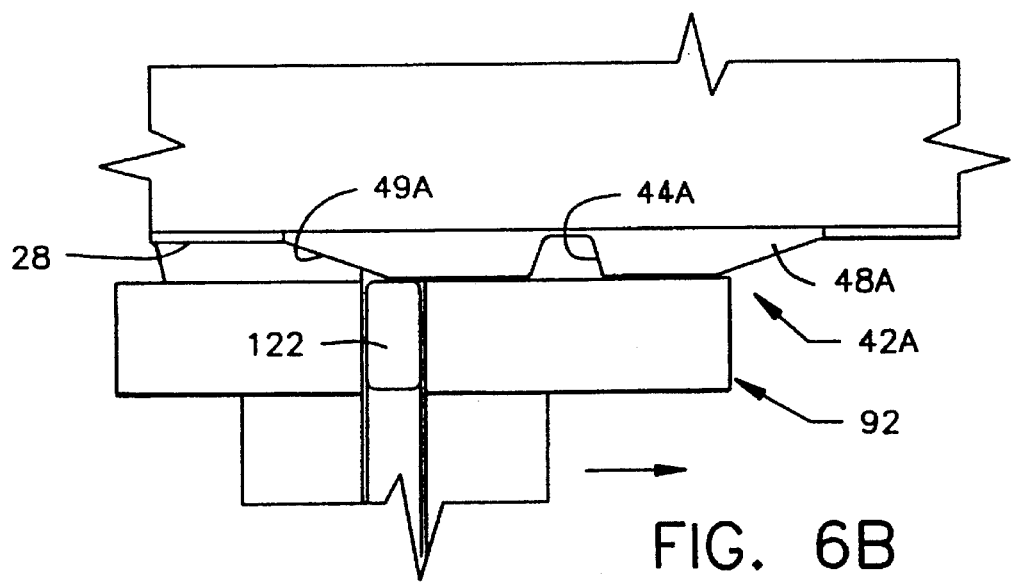
Figure 6C:
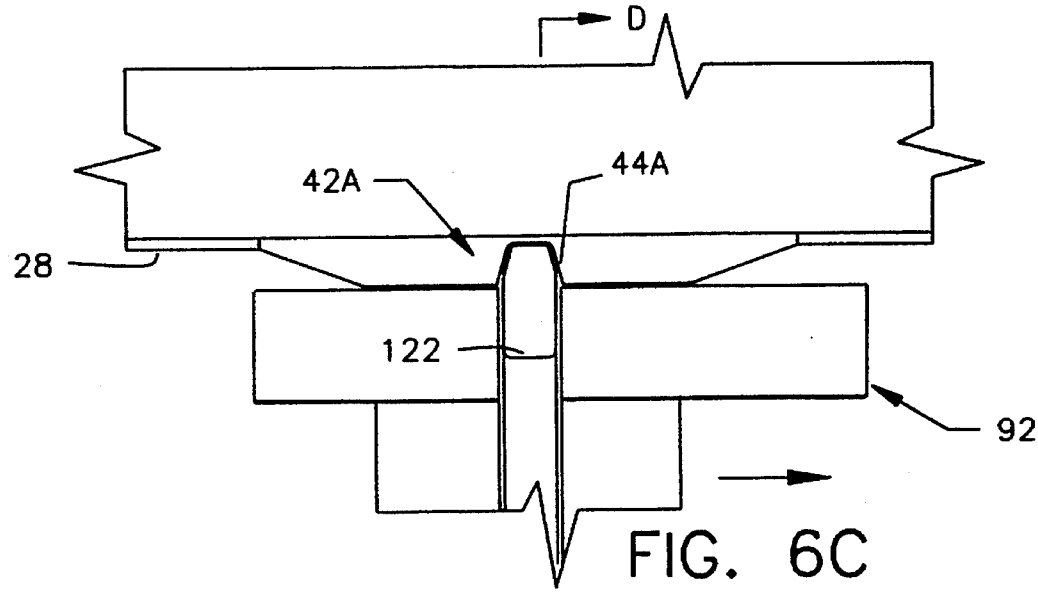

In the sequence shown in FIG. 6B, the locking pin 122 has completed its movement up inclined surface 49A and is now riding along track rim surface 46A. At this point, the pivoting locking leg has fully pivoted into the unlocked position.

Figure 7A:
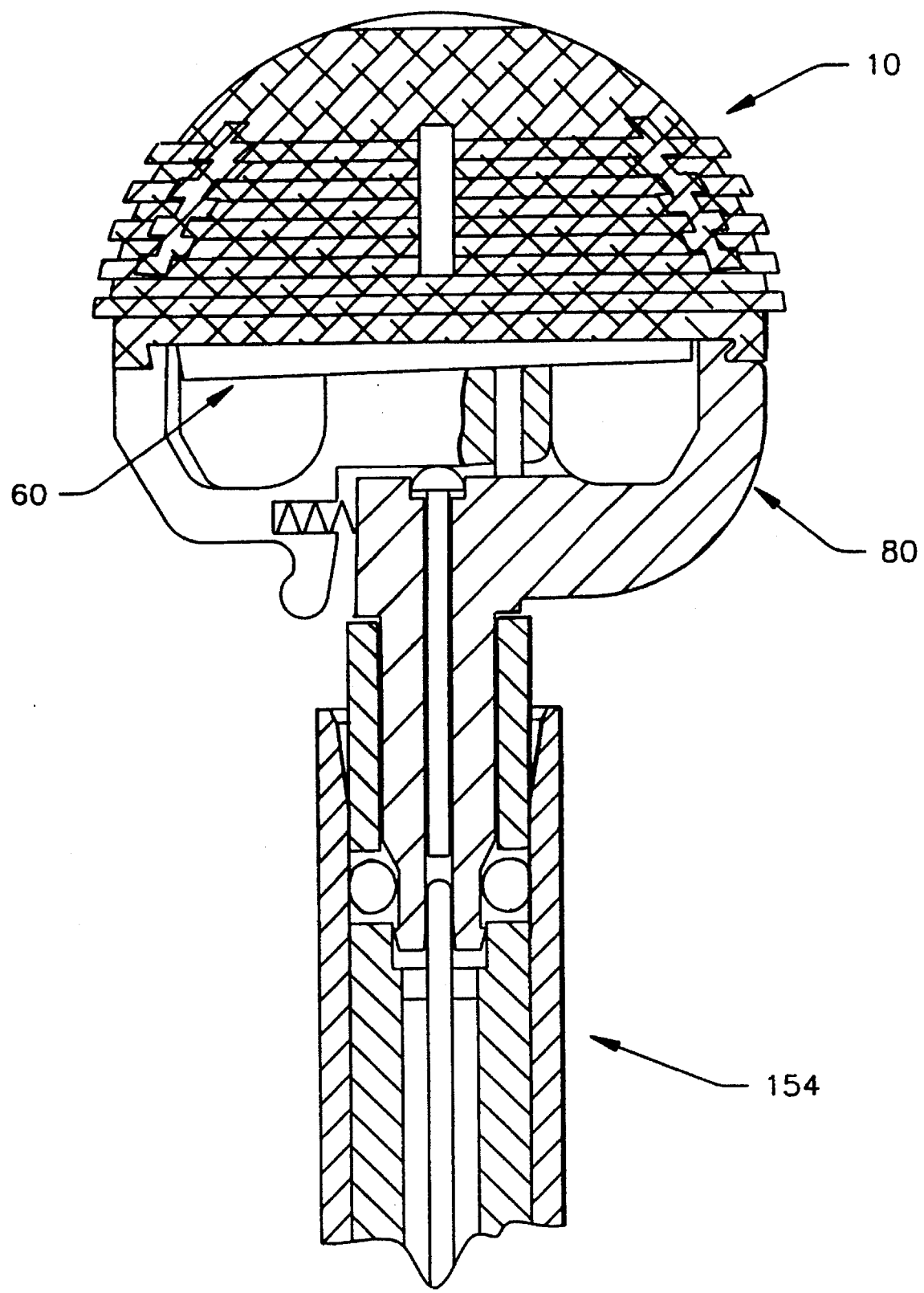
FIG. 7A is a partial cross-sectional assembled view of acetabular cup, cup adaptor and impactor tool.

In the final sequence shown in FIG. 6C, the locking pin 122 moves into depression 44A. This occurs, when the pivoting leg return spring forces the pivoting locking leg back into the locked position thereby causing the locking pin 122 to move into depression 44A. Once pivoting pin 122 is in depression 44A, the cup adaptor can not be rotated relative to the cup. The fully coupled acetabular cup/cup adaptor/IPT assembly can be seen in FIG. 7A.

The acetabular cup, using the impactor, is placed at the entrance to the acetabular socket where the alignment of the cup is checked and confirmed using the impactor. Once alignment and position are established, the acetabular cup is impacted into the acetabulum using a mallet (not shown) on the end of handle grip of the impactor.

Once the acetabular cup is fully seated within the acetabulum, the cup adaptor is uncoupled for the acetabular cup. In order to release the cup from the cup adaptor, one slides the cup releasing collar toward the first end (coupling end) of the IPT as shown in FIG. 7B. This causes the cup releasing rod to engage and move the actuating pin of the cup adaptor which thereby pivots the pivoting arm into the unlocked position such that the locking pin is no longer seated in the depression. The cup adaptor and IPT are then rotated relative to the cup along the base surface until the track receiving sections disengage from the locking tracks of the cup. Once disengagement occurs, the cup adaptor/IPT can be removed from the acetabular cup.

To release the cup adaptor from the IPT, one merely slides the retaining collar 156 of the IPT toward the hand grip while removing the chuck of the adaptor assembly from the coupling means.

Although the preferred embodiments of the acetabular cup 10, the adaptor cup 80 and the impactor tool 150 described above are designed to replace the human hip acetabulum, modifications of these devices to render them suitable in other applications such as the shoulder or the like, will become apparent to those skilled in the art.

Thus, these and other variations or modifications to the invention described herein are intended to be included within the scope of the invention as defined by the appended claims.

I/We claim:

1. A tool for installing an acetabular cup having an outer shell of a hard material with a cavity circumscribed by a peripheral surface, and a bearing insert of a material which is softer than said material of said outer shell disposed within said cavity of said shell, said tool comprising:

handle means for aligning and driving the acetabular cup into said acetabulum;

adaptor means for coupling said handle means to said acetabular cup, said adaptor means having leg means for engaging corresponding leg receiving means positioned on the peripheral surface of the outer shell when said leg means are brought into contact with the peripheral surface of the outer shell and said adaptor means is rotated relative to said acetabular cup, said leg means including a pair of substantially parallel oriented leg members unitarily formed with said adaptor means, and locking means for preventing relative rotation between said adaptor means and the acetabular cup when said leg means of said adaptor means are engaged with the leg receiving means of the outer shell, said locking means being slidably oriented between said pair of leg members.

2. The tool according to claim 1, wherein said handle means includes release means for deactivating said locking means of said adaptor means and allowing relative rotation between said adaptor means and the acetabular cup so that said legs means of said adaptor means can be disengaged form the leg receiving means of the outer shell.

3. The tool according to claim 1, wherein said handle means further includes assist handle means for aligning said cup within said acetabulum.

4. The tool according to claim 1, wherein said adaptor means further includes chuck means and said handle means further includes chuck receiving means, said chuck means on said adaptor means and said chuck receiving means on said handle means coacting to couple and uncouple said adaptor means and said handle means.

5. The tool according to claim 1, wherein said adaptor means further includes indicia means, said indicia means allowing said adaptor to be selectively matched by size with a corresponding acetabular cup.

\* \* \* \* \*